United States Patent [19]
Tumibay

[11] Patent Number: 5,439,465
[45] Date of Patent: Aug. 8, 1995

[54] BONE COMPRESSION AND DISTRACTION SURGICAL TOOL

[76] Inventor: Delfin O. Tumibay, 36 Armstrong Dr., Clark, N.J. 07066

[21] Appl. No.: 209,080
[22] Filed: Mar. 11, 1994
[51] Int. Cl.⁶ ............................................. A61B 17/56
[52] U.S. Cl. ................................................... 606/105
[58] Field of Search .............. 606/90, 105; 269/244, 269/251

[56] References Cited

U.S. PATENT DOCUMENTS

| | | | |
|---|---|---|---|
| 1,904,798 | 4/1933 | Nurnberger | 269/244 |
| 2,317,195 | 4/1943 | Husted | 269/244 |
| 3,709,219 | 1/1973 | Halloran | 606/105 |
| 4,187,841 | 2/1980 | Knutson . | |
| 4,779,857 | 10/1988 | Maund | 269/244 |

FOREIGN PATENT DOCUMENTS 7288 of 1890 United Kingdom ................ 269/244

*Primary Examiner*—Tamara L. Graysay
*Attorney, Agent, or Firm*—Frank Cozzarelli, Jr.

[57] ABSTRACT

According to the present invention a bone compression or distraction surgical tool is provided, which comprises: a male threaded shaft that extends through a housing having a relatively long slot running parallel to the shaft from a first end of the housing and a relatively short slot running parallel to the shaft from a second end of the housing, these slots being in line with one another; a fixed arm having on one end an internally smooth sleeve, which surrounds the shaft, said arm extending through the short slot; a movable arm having, on one end, a female threaded sleeve, which surrounds the shaft and engages the male threads thereof, and extending through the long slot; and a handle for rotating the shaft, the rotation of which moves the movable arm via the threaded connection. Both the fixed arm and the movable arm have a hole for attaching surgical pin apparatus at the end of each arm as well as to the bone ends so the bones may be moved as required by the movement of the movable arm.

14 Claims, 3 Drawing Sheets

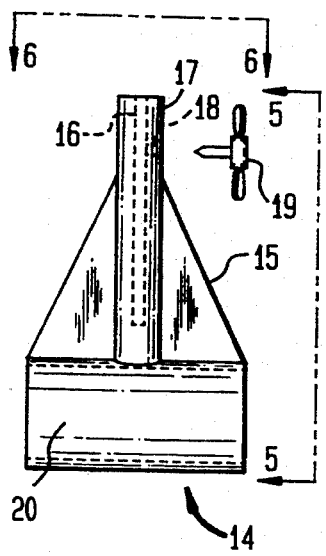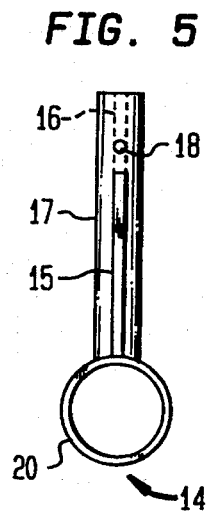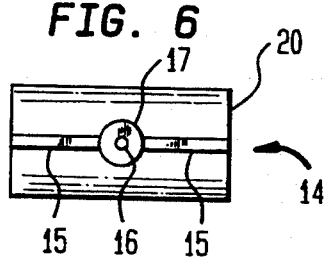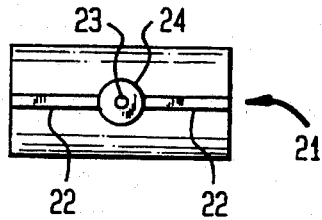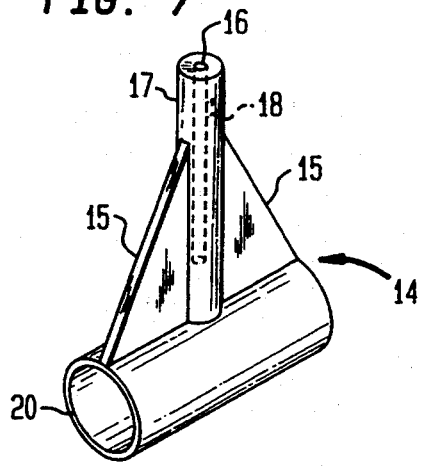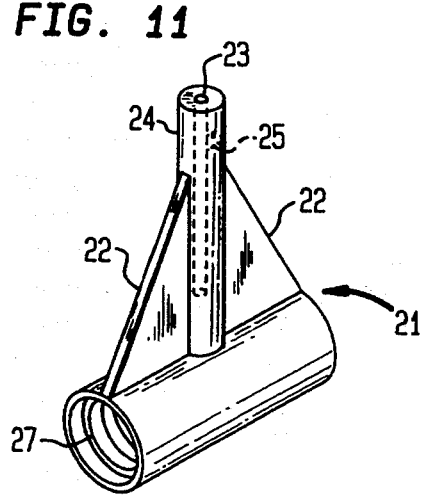

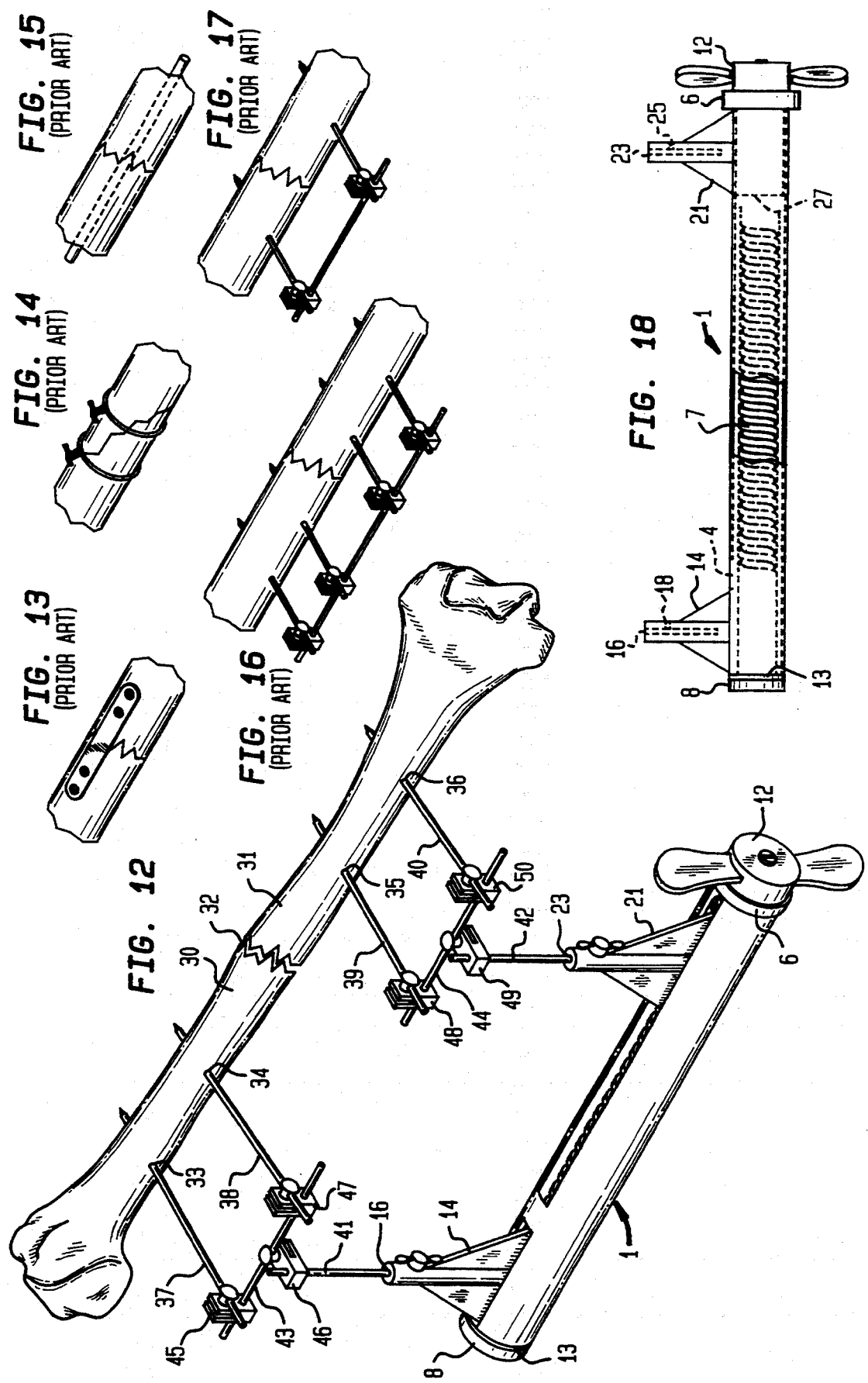

BONE COMPRESSION AND DISTRACTION SURGICAL TOOL

TECHNICAL FIELD

This invention relates to surgical tools and, more particularly is directed toward a device that may be used to either compress or distract a bone fracture during fixation.

BACKGROUND OF INVENTION

Healing of a bone fracture may be enhanced by using various compression or distraction devices or tools that hold the fractured bone together. Such tools typically utilize, for example, a bone plate that must be secured to both sides of the fracture by pins, clamps or screws. Other methods of improving bone fracture healing may be used such as intramedullary pinning, which is a pin inserted longitudinally through the bone sections; by cerclage wiring around the fracture; by external pin fixation; and by various configurations using well known and commonly available from medical supply firms Kirschner's clamps and pins.

To successfully apply such devices during surgery and to properly seat the bone portions, it is necessary to compress the bone, and/or distract and then compress the bone, depending on the type of fracture. After compression, distraction, or both, the bone must be held immobile while the plate or other devices listed above are being installed; and kept in place during the subsequent healing process.

Presently, various bone hooks and clamps are utilized for compression and/or distraction. Some clamps partially encircle both bone portions and then attempt to apply linear force to compress the same. Disadvantages of such bone encircling clamps are that, due to the applied pressure, the bone may break, or the clamp may slip. Further, it is extremely difficult, with the prior art devices, to apply a solid and steady compressive force, which is defined as forcing the bone ends together to minimize any gap between them, prior to fixation.

For distraction, which is defined as the elimination of the bone overlap, bone hooks are commonly used but they require the use of two hands to apply them. Due to their disjunctive nature, such hooks provide uneven, unsteady forces that are difficult to manipulate and control. There are other distraction devices that are complicated and also difficult to use.

Accordingly, it may be appreciated that the prior art bone compression and distraction tools have been difficult to control; generally are complex in construction; require two hands for proper manipulation; do not provide an even, steady application of force in the proper direction; require relatively large incisions; and are equally difficult to install as to remove.

The present invention relates to a simplified but versatile surgical tool that may be used to either compress or distract a bone fracture and to facilitate reduction or alignment of the broken bone prior to fixation.

Prior art U.S. patents in the general area of which I am aware include: U.S. Pat. No. 4,782,842 and 4,187,841.

DISCLOSURE OF THE INVENTION

An object of the present invention, therefore, is to provide a new and improved bone compression and distraction surgical tool, which facilitates installation.

Other objects and advantages will become apparent hereinafter.

According to the present invention a bone compression or distraction surgical tool is provided, which comprises: a male threaded shaft that extends through a housing having a relatively long slot running parallel to the shaft from a first end of the housing and a relatively short slot running parallel to the shaft from a second end of the housing, these slots being in line with one another; a fixed arm having on one end an internally smooth sleeve, which surrounds the shaft, said arm extending through the short slot and having means for attaching surgical pin apparatus at the other end of the arm; a movable arm having, on one end, a female threaded sleeve, which surrounds the shaft and engages the male threads thereof, said arm extending through the long slot and having means for attaching surgical pin apparatus at the other end of the arm; and means for rotating the shaft, the rotation of which moves the movable arm via the threaded connection.

BRIEF DESCRIPTION OF THE DRAWINGS

FIG. 4 is a front view of the fixed arm;

FIG. 5 is a side view of fixed arm of FIG. 4;

FIG. 6 is a top view of the fixed arm of FIG. 4;

FIG. 7 is a perspective view of the fixed arm of FIG. 4;

FIG. 8 is a front view of the movable arm;

FIG. 9 is a side view of movable arm of FIG. 8;

FIG. 10 is a top view of the movable arm of FIG. 8;

FIG. 11 is a perspective view of the movable arm of FIG. 8;

FIG. 12 is a perspective view which illustrates the use of the surgical tool of FIG. 3 prior to the installation of the securing device for example, a bone plate, etc.;

FIG. 13 is a perspective view which illustrates the attachment of a prior art bone plate bone securing device after the use of the surgical tool of FIG. 12;

FIG. 14 is a perspective view which illustrates the attachment of a prior art cerclage wire bone securing device after the use of the surgical tool of FIG. 12;

FIG. 15 is a perspective view which illustrates the attachment of a prior art intramedullary pinning bone securing device after use of the surgical tool of FIG. 12;

FIG. 16 is a perspective view which illustrates the attachment of a prior art four pin external pin fixation bone securing device after the use of the surgical tool of FIG. 12;

FIG. 17 is a perspective view which illustrates the attachment of a prior art two pin external pin fixation bone securing device after use of the surgical tool of FIG. 12; and FIG. 18 is a side view of the assembled bone compression and distraction surgical device showing a portion of the male threaded, cylindrical, shaft with a fixed arm attached to the housing.

DESCRIPTION OF THE PREFERRED EMBODIMENT(S)

Figure 1:
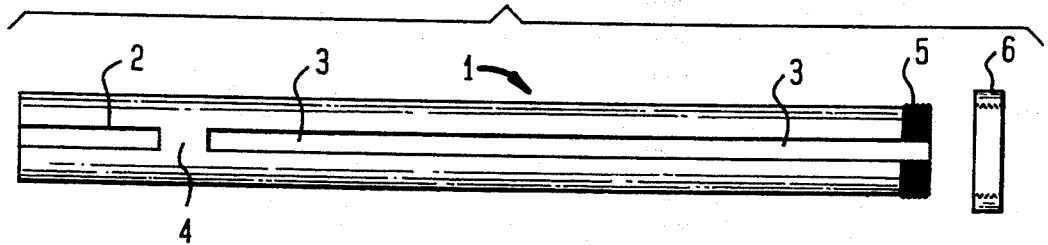
FIG. 1 is a plan view of a preferred embodiment of the housing.

Referring to the drawings, wherein like reference numbers represent identical or corresponding parts throughout the several views, and more particularly to FIGS. 1 through 18 thereof, is shown one preferred embodiment of the present invention which is utilized in either bone compression or distraction. FIGS. 13 through 17 shown various ways of attaching means for securing the bone portions after having used the tool of the present invention.

The bone compression or distraction surgical tool includes a housing 1; male threaded, cylindrical, rigid shaft 7; a fixed arm 14; a movable arm 21; end cap 6; winged handle 12; and washer 13. Rotation of winged handle 12 will, in turn, rotate threaded, cylindrical, rigid shaft 7 which in turn will cause movable arm 21 to move longitudinally on the threaded, cylindrical, rigid shaft and through slot 3 in housing 1. This action will cause the compression or distraction of the broken bone portions depending on the direction of rotation of winged handle 12. Although a winged handle is shown a wrench may also be used to rotate the rigid shaft.

Said housing 1 of the bone compression or distraction surgical tool includes a longitudinal slot 2 starting at one end, up to solid section 4 and continuation of the longitudinal slot 3 to the opposite end of the housing 1 which has an externally threaded section 5. Slots 2 and 3 are in line with each other. End cap 6 has female threads so it can be screwed on to the end of housing 1 to retain the cylindrical, threaded, rigid shaft 7. Various other details of the bone compression or distraction surgical tool will be described in the assembly that follows.

One way to assemble the bone compression or distraction surgical tool of the present invention is to insert threaded, cylindrical, rigid shaft 7 into washer 13 and then into unthreaded, cylindrical section 20 of fixed arm 14 and then into housing 1 until the flange 8 of the cylindrical, threaded, rigid shaft 7 is in contact with washer 13 and the housing 1. The threaded, cylindrical section 27 of movable arm 21 is inserted on to the hexagonal end 10 of threaded, cylindrical, rigid shaft 7 and rotation of either the rigid shaft 7 by means of flange 8 or hexagonal end 10 will cause the movable arm 21 to move into slot 3. When the movable arm 21 is positioned well into the slot 3, end cap 6 is screwed on the end of the housing 1 from which the hexagonal end 10 of threaded, cylindrical, rigid shaft 7 protrudes. Then winged handle 12 is placed over the hexagonal end 10 which has a matching hexagonal opening 11 and then secured with screw 29. This completes one method of assembling the bone compression or distraction surgical tool. Other variations of assembly may be used.

All pieces of the bone compression or distraction surgical tool of the present invention should be constructed of stainless steel, to facilitate cleaning and sterilization. Other materials of construction may be used including nonmetallic materials such as plastics. There are few moving parts and the simplicity in construction minimizes buildup of foreign material and thereby facilitates use, cleaning and proper sterilization. Various sizes of pins 37, 38, 39, and 40 permit use of the same tool on both large and small bones. Although a preferred use of the bone compression or distraction surgical tool of the present invention is by veterinarians as a tool to repair broken bone of animals such as, but not limited to, dogs and cats, it may also be used on larger animals and even human beings.

Referring to FIG. 12, in the operation of the embodiment shown four pins 37, 38, 39 and 40 are used to secure the bone portions 30 and 31 shown separated by a bone fracture 32. After appropriate administration of anesthesia, the position of the broken bone pieces are evaluated. If traction is necessary to oppose the ends of the broken bone pieces, which usually occur in a fracture of long bones, the bone compression or distraction surgical tool is applied. When it is elected to incise the skin, incision(s) are made in the animal's leg or other body part, the skin, fat, muscle, etc. is separated to expose the bone portions, and appropriately sized holes 33, 34, 35 and 36 are drilled through the cortex of the bone as far as possible from the break 32 in each bone portion 30 and 31. It is not always needed to incise the skin, because the broken bone may be set by merely puncturing the skin and attaching the surgical tool of the present invention. Likewise, it is not always necessary to drill holes such as 33, 34, 35, and 36 because pins may be inserted and rotated as they are inserted to penetrate the bone.

After assembly of the bone compression and distraction surgical tool of the present invention and as described herein, the fixation pin assembly, for example, shown in FIG. 12 but not limited to that assembly, is prepared, preferably prior to surgery, by inserting pin 41 into aperture 16 of fixed arm 14 and pin 42 into aperture 23 in movable arm 21. Pin 41 is inserted vertically into one hole in Kirschner clamp 46 and pin 43 is inserted into a bolt in said Kirschner clamp 46 which has a hole in it to receive pin 43. Pins 41 and 43 are at right angles to each other. Pin 43 is inserted into Kirschner clamp 45 and the opposite end of pin 43 is inserted into Kirschner clamp 47 which has a hole in it to receive pin 43. Pin 37 is inserted into Kirschner clamp 45 which is inserted into a bolt in said Kirschner clamp 45 which has a hole in it to receive pin 37. Likewise pin 38 is inserted into Kirschner clamp 47 which is inserted into a bolt which has a hole in said Kirschner clamp 47 which has a hole in it to receive pin 38. Pins 37 and 38 may be at right angles to pin 43 and they may be but are not necessarily parallel to each other. Usually, they are at an angle to each other. Kirschner clamps are commonly used in the medical profession.

Pins 41 and 42 may be of various diameters up to about the diameter of apertures 16 and 23. Thus, various size pins will accommodate various restructuring and repairing of bones of various sizes and dimensions from "small" to "large" bones in various animals and human beings.

Similarly, the fixation pin assembly at the opposite end of the bone compression and distraction surgical tool of the present invention and as described herein and shown in FIG. 12, is prepared, preferably prior to surgery, by inserting pin 42 into aperture 23 of movable arm 21. Pin 42 is inserted vertically into one hole in Kirschner clamp 49 and pin 44 is inserted into a bolt in said clamp which has a hole in it to receive pin 44. Pins 42 and 44 may be at any angle to each other. Pin 44 is inserted into Kirschner clamp 48 and the opposite end of pin 44 is inserted into Kirschner clamp 50 which has a hole in it to receive pin 44. Pin 39 is inserted into Kirschner clamp 48 which is inserted into a bolt in said Kirschner clamp 48 which has a hole in it to receive pin 39. Likewise Pin 40 is inserted into Kirschner clamp 50 which is inserted into a bolt which has a hole in said clamp which has a hole in it to receive pin 40. Pins 39 and 40 may be at any angle to pin 44 and they may be but are not necessarily parallel to each other. Usually they are at an angle to each other. Once the temporary fixation pin assembly to be used with the bone compression or distraction surgical tool of the present invention is assembled, as shown in FIG. 12, for example, then pin 37 is inserted into hole 33, pin 38 is inserted into hole 34 of bone portion 30 and pin 39 is inserted into hole 35 and pin 40 is inserted into hole 36 of the bone portion 31. The surgeon may prefer to insert pins 37, 38, 39 and 40 first and reverse the assembly as described, regardless of the angularity of the pins to each other. The Kirschner clamp will adjust for any deviation in angularity of the pins. It is possible and sometimes preferable to insert only one pin in each bone portion as shown in FIG. 17 rather than the two pin assembly of FIG. 12. The choice is the surgeon's.

Once the bone compression or distraction surgical tool of the present invention and the temporary external fixation assembly are in place, prior to the proper positioning of the bone portions 30 and 31, winged handle 12 is rotated to first distract, which is the elimination of the bone overlap by drawing the bone portions apart. This approximately aligns the bone portions 30 and 31. Once the bone portions are almost aligned, winged handle 12 is rotated in the opposite direction from that used to distract the bone portions in order to compress the bone portions 30 and 31 until the fracture 32 is in the best possible alignment depending on the bone fracture, thus completing the seating of the bone portions 31 and 32 which are ready to be secured for the healing process. It should be noted that the muscles and tendons after a fracture are contracted and the natural body reaction is used to assist in the final alignment and seating of the bone portions.

Winged handle 12 is rotated manually but it may also be rotated with a wrench or other tool. Manual rotation is preferred, although a very slow speed motorized tool could be used to rotate said winged handle.

After proper compression and seating of the bone portions, the bone compression or distraction surgical tool of the present invention will hold the bone portions in place while an appropriate device, similar to those in FIGS. 13 through 17, is attached to the bone portions 30 and 31 to secure them during the extended healing process. The versatility of bone compression or distraction surgical tool of the present invention is clearly shown in that it can accommodate various devices to secure the bone portions as shown but not limited to the bone plate FIG. 13, cerclage wiring FIG. 14, intramedullary pinning FIG. 15, and various Kirschner clamps and pin arrangements such as FIG. 16 and FIG. 17.

After attaching the device of choice to the bone portions 30 and 31 to secure them during the extended healing process, the bone compression or distraction surgical tool of the present invention is removed. The surgeon then properly closes the various incisions and the healing process begins.

Once the bone compression or distraction surgical tool of the present invention is attached, the surgeon can have both hands free to continue the necessary surgical procedures. This is possible because the tool will not move, unless the surgeon wants to make an adjustment, once it is assembled prior to the attachment of the temporary fixation device and during the entire surgical procedure. Another major advantage is clear in that the distraction and compression of the bone portions is easily accomplished by merely rotating winged handle 12 first in one direction to distract and in the opposite direction to compress. The surgeon's hands are free to do the surgical procedure without fear that the assembly will slip or move.

Another embodiment of the present invention is shown in FIG. 18 wherein a modified fixed arm 14 is attached to the outer surface of housing 1 in line with slot 3 and movable arm 21. This makes the fixed arm a part of housing 1. The height of fixed arm 14 is the same as that of movable arm 21. Assembly of this embodiment is similar to that previously described except that there is no smooth sleeve 20.

Obviously, numerous modifications and variations of the present invention are possible in light of the teachings disclosed herein. Bone distractions or compression can be done on human beings and animals and on various bones, for example: legs, ribs, arms, hands and others. Therefore, it is to be understood that within the scope of the following claims the invention may be practiced otherwise than as specifically described herein.

In order to give some indication of the size of the bone compression and distraction surgical tool of the present invention, some of, but not limited to, the approximate dimensions for one of the embodiment shown in FIG. 12 follow.

Housing 1 of FIG. 1 may be about one inch nominal inside diameter by about fourteen inches long. The longitudinal slot portion of housing 1 is about 7/16 inch in width by about one and one half inches in length followed by a solid section 4 that may be about one inch in length that is followed by slot 3 that is about 7/16 inch in width and eleven and one half inches in length to the end of said housing 1. Housing 1 is threaded at section 5 on which is screwed cap 6.

Figure 2:
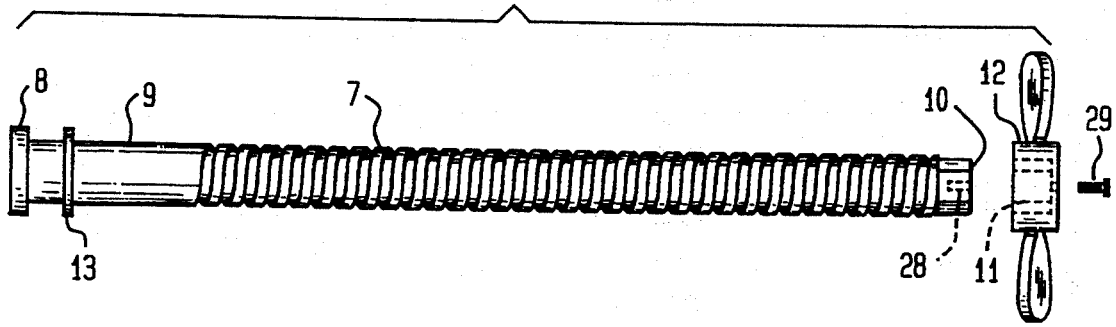
FIG. 2 is a plan view of the male threaded, cylindrical, shaft.
Figure 2A:
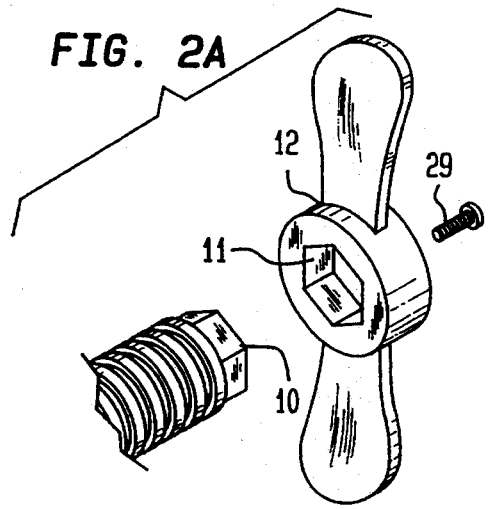
FIG. 2A is a perspective view of the end of the threaded, cylindrical, shaft and winged handle (rotation device)
Figure 3:
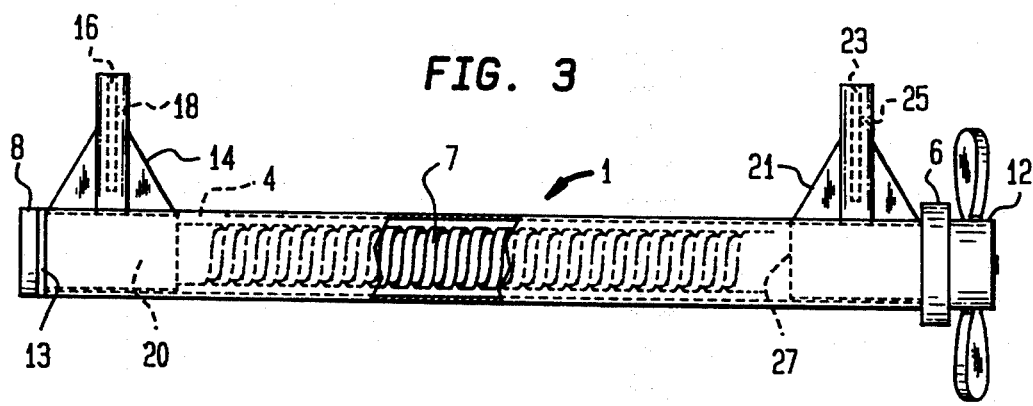
FIG. 3 is a side view of the assembled bone compression and distraction surgical device showing a portion of the male threaded, cylindrical, shaft.

The cylindrical, male threaded, rigid shaft of FIG. 2 has an outside diameter of about ½ inch and is about twelve inches long. Flange 8 is about one inch in diameter so that it will be held at the end of housing 1. There is an unthreaded section 9 on cylindrical, threaded, rigid shaft of FIG. 2 that is as long as the unthreaded cylindrical section 20 of fixed arm 14. Thus rotation of said cylindrical, threaded, rigid shaft of FIG. 2 will not cause fixed arm 14 to move. The threaded section 7 of cylindrical, threaded, rigid shaft of FIG. 2 extends to the end of the rigid shaft except for the hexagonal end 10 of FIG. 2 and 2A which is about ½ inch wide by about ¼ inch wide and about ¼ inch in depth. Winged handle 12 in FIG. 2A is about ½ inch in diameter and has a matching hexagonal section 11 shown in FIG. 2A that matches hexagonal section 10. When cap 6 is secured to section 10 by engaging the hexagonal sections 10 and 11 and by screwing screw 29 through the cap 6 and rigid shaft section 10, rotation of the winged handle 12 will cause the movable arm 21 to move on said shaft threaded section 7.

Fixed arm 14, shown in FIG. 4, 5, 6 and 7, has an unthreaded section 20 of about ⅞ inch outside diameter, by about one and half inch in length with vertical end 17 that is about two inches in length with an aperture 16 about ⅜ inch in diameter extending vertically downward essentially to, but just short of, cylindrical section 20 to receive pin 41 of various diameters up to the diameter of said aperture 16. Winged handle 19 is screwed into screw hole 18 in fixed arm 14 at essentially a right angle to said vertical end 17 of fixed arm 14 until it enters one side of aperture 16. The winged handle 19 is used to secure pins placed into aperture 16. Gusset 15 is used to add strength to fixed arm 14.

Movable arm 21, shown in FIG. 8, 9, 10 and 11 has a female threaded, cylindrical section 21 of about ¾ inch outside diameter by about one and one half inches in length with vertical end 24. The female threads 27 of the movable arm 21 match the male threads 7 of cylindrical, rigid shaft, FIG. 2. Vertical section 24 is about two inches in length with an aperture 23 about ⅜ inch in diameter extending vertically downward essentially to, but short of, threaded cylindrical section 27 to receive pin 42 of various diameters up to the diameter of said aperture 23. The winged handle 26 is used to secure pins placed into aperture 23. Winged handle 26 is screwed into screw hole 25 in movable arm 21 at essentially a right angle to said vertical end 24 of movable arm 21 until it enters one side of aperture 23. Gusset 22 is used to add strength to movable arm 21.

The present invention is a versatile surgical tool because it allows the surgeon to apply various bone securing techniques for proper healing of bone fractures including but not limited to bone plating, cerclage wiring of the bone, intramedullary pinning, and various external fixation systems using Kirschner clamps and pins apparatus.

A number of additional advantages relating to the use of the bone compression and distraction surgical tool of the present invention follow.

1. A surgical tool, which may be utilized either for bone compression or distraction with equal facility, and does not require encircling of the bone.
2. A bone compression and distraction surgical tool that holds the bone solidly, allows the surgeon to have two hands free, allows free access to other bone surfaces, and provides even and steady forces in either compression and distraction.
3. A unique bone compression and distraction surgical tool which is of simple construction, is durable, easy to clean, may be used on either small or large bones, provides firm bone contact and hold during use, and permits easy adjustment during use for a precise fit.
4. An inexpensive bone compression or distraction surgical tool which lessens soft tissue exposure, bone damage, and thereby will reduce potential infection.
5. A surgical tool that can accommodate various sizes of pins for the fixation of broken bones.
6. A surgical tool that can accommodate different configurations of pin holders.
7. A surgical tool that permits, for example but not limited to, application of bone plates, cerclage wiring, intramedullary pinning, various external fixation configurations with Kirschner's clamps and pins and other devices to broken bones.
8. A surgical tool that allows for the application of a connecting rod to the bone after which the surgical device is removed.
9. A surgical tool that allows for the attachment of pins to the broken bone at a point furthest away from the break to avoid any additional breaking of the bone ends nearest the break.

Alternative embodiments and modes of practicing the invention, but within the spirit thereof, will, in the light of this disclosure, occur to persons skilled in the art. It is intended, that this description be taken as illustrative only and not be construed in any limiting sense.

I claim:

1. A bone compression or distraction surgical tool comprising:
   i. a rigid male threaded shaft;
   ii. a housing surrounding said shaft having a relatively long slot running parallel to the shaft from a first end of the housing and a relatively short slot running parallel to the shaft from a second end of the housing, said slots being in line with one another;
   iii. a fixed arm having on one end an internally smooth sleeve, which surrounds the shaft, said arm extending through the short slot and having means for attaching surgical pin apparatus at the other end of the arm;
   iv. a movable arm having, on one end, a female threaded sleeve, which surrounds the shaft and engages the male threads thereof, said arm extending through the long slot and having means for attaching surgical pin apparatus at the other end of the arm; and
   v. means for rotating the shaft, the rotation of which moves the movable arm via the threaded connection.

2. The bone compression and distraction surgical tool as set forth in claim 1, wherein said rotation means is a winged handle which is attached to the end of the rigid shaft with a screw.

3. A bone compression and distraction surgical tool, which comprises:
   i. a male threaded, cylindrical, rigid shaft extending through a fixed arm having an unthreaded, cylindrical sleeve and extending through and rotatably engaged with a longitudinally movable arm having an internally female threaded cylindrical sleeve;
   ii. a housing surrounding said threaded, cylindrical rigid shaft and said sleeves, said housing having a longitudinal slot to allow said fixed arm and said movable arm to protrude in the same direction therethrough;
   iii. rotation means attached to a first end of said cylindrical, rigid shaft; and
   iv. first retaining means at each end of said cylindrical, rigid shaft.

4. The bone compression and distraction surgical tool as set forth in claim 3 wherein said movable arm with the internally threaded cylindrical sleeve is positioned along said shaft by said rotation means and serves as the compression and distraction surgical tool.

5. The bone compression and distraction surgical tool as set forth in claim 3 wherein said slot comprises a first slot, which extends for a threaded length of the rigid shaft and a second slot which extends for a length of the fixed arm, and the slots being in line with one another.

6. The bone compression and distraction surgical tool as set forth in claim 3, wherein said fixed arm sleeve has an unthreaded inner substantially cylindrical surface having a diameter larger than said threaded cylindrical, rigid shaft and an outside diameter smaller than an inside diameter of said housing.

7. The bone compression and distraction surgical tool as set forth in claim 8 wherein said fixed arm has a smooth hole of desired depth extending perpendicular to the cylindrical surface.

8. The bone compression and distraction surgical tool as set forth in claim 7 wherein said smooth hole is provided with a threaded hole perpendicular thereto into which is inserted a second retaining means to secure a pin inserted into the hole.

9. The bone compression and distraction surgical tool as set forth in claim 3, wherein said movable arm sleeve has a threaded internal cylindrical surface in which female threads rotatably engage the male threads of said rigid shaft and an outside diameter smaller than an inside diameter of said housing.

10. The bone compression and distraction surgical tool as set forth in claim 9 wherein said movable arm has a smooth hole of desired depth extending perpendicular to the threaded internal cylindrical surface.

11. The bone compression and distraction surgical tool as set forth in claim 10 wherein said smooth hole is provided with a threaded hole perpendicular thereto into which is inserted a second retaining means to secure a pin inserted into the smooth hole.

12. The bone compression and distraction surgical tool as set forth in claim 3, wherein said first retaining means at one end of said threaded cylindrical, rigid shaft is a flange including a washer, and said first retaining means at the opposite end of said threaded cylindrical, rigid shaft is a female threaded cap screwed on to a thread end of said housing.

13. The bone compression and distraction surgical tool as set forth in claim 3, wherein said cylindrical, rigid shaft has a hexagonal cross-section at said first end and said hexagonal first end having a threaded hole to accommodate a matching screw.

14. The bone compression and distraction surgical tool as set forth in claim 13, wherein said rotation means is a winged handle having a hexagonal cross-section opening matching the hexagonal cross-section first end of the rigid shaft, said winged handle is attached to the rigid shaft with said screw.

* * * * *